(12) United States Patent
Izatt et al.

(10) Patent No.: US 10,835,119 B2
(45) Date of Patent: Nov. 17, 2020

(54) COMPACT TELESCOPE CONFIGURATIONS FOR LIGHT SCANNING SYSTEMS AND METHODS OF USING THE SAME

(71) Applicant: Duke University, Durham, NC (US)

(72) Inventors: Joseph A. Izatt, Durham, NC (US); Francesco Larocca, Durham, NC (US); Theodore Dubose, Durham, NC (US); Derek Nankivil, Durham, NC (US)

(73) Assignee: Duke University, Durham, NC (US)

( * ) Notice: Subject to any disclaimer, the term of this patent is extended or adjusted under 35 U.S.C. 154(b) by 6 days.

(21) Appl. No.: 15/547,547

(22) PCT Filed: Feb. 5, 2016

(86) PCT No.: PCT/US2016/016900
§ 371 (c)(1),
(2) Date: Jul. 31, 2017

(87) PCT Pub. No.: WO2016/127140
PCT Pub. Date: Aug. 11, 2016

(65) Prior Publication Data
US 2018/0271367 A1    Sep. 27, 2018

Related U.S. Application Data

(60) Provisional application No. 62/112,389, filed on Feb. 5, 2015.

(51) Int. Cl.
*A61B 3/12* (2006.01)
*A61B 3/10* (2006.01)
*A61B 3/13* (2006.01)

(52) U.S. Cl.
CPC ............ *A61B 3/1208* (2013.01); *A61B 3/102* (2013.01); *A61B 3/1025* (2013.01); *A61B 3/13* (2013.01); *A61B 3/12* (2013.01)

(58) Field of Classification Search
None
See application file for complete search history.

(56) References Cited

U.S. PATENT DOCUMENTS 5,040,229 A    8/1991   Lee et al.
5,483,364 A    1/1996   Ishimoto et al.
(Continued)

FOREIGN PATENT DOCUMENTS

EP      1647370 A1     4/2006
KR   1020130000023    1/2013
(Continued)

OTHER PUBLICATIONS

Non-Final Office Action issued in counterpart U.S. Appl. No. 15/547,537 dated Jun. 1, 2018.
(Continued)

*Primary Examiner* — Darryl J Collins
*Assistant Examiner* — Journey F Sumlar
(74) *Attorney, Agent, or Firm* — Olive Law Group, PLLC

(57) ABSTRACT

Compact telescope configurations for light scanning systems and related methods are disclosed. According to an aspect, a system for imaging or relaying an image of an object includes a first optical element having a first focal length $f_1$ for imaging or relaying an image of an object at the distance $f_1$ from the first optical element. The system also includes a second optical element having a second focal length $f_2$ for receiving an image of the object from the first optical element and for focusing an output of the image at the distance $f_2$ from the second optical element on a side that opposes the first optical element. The first optical element and the second optical element are separated by a distance of approximately [Formula I], wherein r is the finite radius of curvature of the wavefront of light located at the object or image of the object.

18 Claims, 11 Drawing Sheets

(56) References Cited

U.S. PATENT DOCUMENTS

| | | | |
|---|---|---|---|
| 5,493,109 | A | 2/1996 | Wei et al. |
| 5,715,081 | A | 2/1998 | Chastang et al. |
| 5,963,301 | A | 10/1999 | Volk |
| 6,671,581 | B2 | 12/2003 | Niemeyer et al. |
| 7,791,794 | B2 | 9/2010 | Reimer et al. |
| 7,839,494 | B2 | 11/2010 | Reimer et al. |
| 7,907,166 | B2 | 3/2011 | Lamprecht et al. |
| 9,207,638 | B2 | 12/2015 | Dubois et al. |
| 2001/0031078 | A1 | 10/2001 | Doane |
| 2002/0099290 | A1 | 7/2002 | Haddad |
| 2005/0270486 | A1 | 12/2005 | Teiwes et al. |
| 2006/0050991 | A1 | 3/2006 | Jerebko et al. |
| 2007/0086647 | A1 | 4/2007 | Grady |
| 2007/0299309 | A1 | 12/2007 | Seibel et al. |
| 2008/0002183 | A1 | 1/2008 | Yatagai et al. |
| 2008/0019587 | A1 | 1/2008 | Wilensky et al. |
| 2008/0030497 | A1 | 2/2008 | Hu et al. |
| 2008/0058704 | A1 | 3/2008 | Hee et al. |
| 2009/0018393 | A1 | 1/2009 | Dick et al. |
| 2009/0060332 | A1 | 3/2009 | Knapp |
| 2009/0131921 | A1 | 5/2009 | Kurtz et al. |
| 2009/0192523 | A1 | 7/2009 | Larkin et al. |
| 2009/0225407 | A1 | 9/2009 | Nakayama et al. |
| 2009/0244485 | A1 | 10/2009 | Walsh et al. |
| 2009/0257065 | A1 | 10/2009 | Hauger et al. |
| 2009/0287223 | A1 | 11/2009 | Pua et al. |
| 2010/0202677 | A1 | 8/2010 | Imamura et al. |
| 2010/0228123 | A1 | 9/2010 | Brennan et al. |
| 2010/0331858 | A1 | 12/2010 | Simaan et al. |
| 2011/0032533 | A1 | 2/2011 | Izatt et al. |
| 2011/0043757 | A1 | 2/2011 | Everett et al. |
| 2011/0122487 | A1 | 5/2011 | Perelman et al. |
| 2012/0092615 | A1 | 4/2012 | Izatt et al. |
| 2012/0184846 | A1 | 7/2012 | Izatt et al. |
| 2012/0307205 | A1 | 12/2012 | Zhou et al. |
| 2013/0010259 | A1 | 1/2013 | Carnevale |
| 2013/0016319 | A1 | 1/2013 | Vohnsen et al. |
| 2013/0135584 | A1 | 5/2013 | Alasaarela et al. |
| 2013/0188140 | A1 | 7/2013 | Bagherinia et al. |
| 2013/0245375 | A1 | 9/2013 | DiMaio et al. |
| 2013/0293838 | A1 | 11/2013 | Makihira et al. |
| 2014/0009741 | A1 | 1/2014 | Levien et al. |
| 2014/0139916 | A1 | 5/2014 | Doi et al. |
| 2014/0142591 | A1 | 5/2014 | Alvarez et al. |
| 2014/0247425 | A1 | 9/2014 | Hammer et al. |
| 2014/0275760 | A1 | 9/2014 | Lee et al. |
| 2014/0307315 | A1 | 10/2014 | Bohn |
| 2014/0368907 | A1 | 12/2014 | Minami |
| 2015/0173846 | A1 | 6/2015 | Schneider et al. |

FOREIGN PATENT DOCUMENTS

| | | | |
|---|---|---|---|
| WO | 2005106786 | A1 | 11/2005 |
| WO | 2012100030 | A2 | 7/2012 |
| WO | 2012109301 | A2 | 8/2012 |
| WO | 2013008033 | A1 | 1/2013 |
| WO | 2013180773 | A1 | 12/2013 |
| WO | 2014068058 | A1 | 5/2014 |

OTHER PUBLICATIONS

"American National Standard for Safe Use of Lasers" American National Standards Institute, Inc. Mar. 16, 2007.

Aschke et a l., "Augmented Reality in Operating Microscopes for Neurosurgical Interventions." IEEE, Mar. 22, 2003, pp. 652-654 (Mar. 22, 2003), p. 652, col. 2; p. 653, col. 2—p. 653, col. 1; Fig 3 [online].

Goncharov, Alexander V. et al.; "Wide-field schematic eye models with gradient-index lens" J. Opt. Soc. Am. A., vol. 24, No. 8/Aug. 2007, pp. 2157-2174.

Bellman, On a Routing Problem, Richard Bellman, vol. XVI, No. 1, The RAND Corporation, pp. 87-90, 1957, U.S.

Bichlmeier, Christoph et al.; "The Tangible Virtual Mirror: New Visualization Paradigm for Navigated Surgery" Chair for Computer Aided Medical Procedures (CAMP), TU Munich, Germany.

Dabov, Kostadin et al., Image Denoising by Sparse 3-D Transform-Domain Collaborative Filtering, IEEE Transactions on Image Processing, vol. 16, No. 8, Aug. 2007.

Dhalla, Al-Hafeez et al., Complex Conjugate Resolved Heterodyne Swept Source Optical Coherence Tomograph) Using Coherenece Revival, Biomedical Optics Express, vol. 3, No. 3, Feb. 24, 2012.

Dijkstra, A Note on Two Problems in Connexion with Graphs, Cambridge University Press, 1897, vol. 13, p. 26-28, U.K.

International Search Report and Written Opinion dated Aug. 16, 2016 from International Application No. PCT/US16/28862.

International Search Report and Written Opinion dated Aug. 12, 2016 from International Application No. PCT/US16/3105.

Elias, P., et al., A Note on the Maximum Flow Through a Network, IRE Transactions on Information Theory, 1956, pp. 117-119.

Fabritius et al., Automated Segmentation of the Macular by Optical Coherence Tomography, Optics Express, vol. 17, No. 18, Aug. 31, 2009, US.

Farsiu et al., Fast Detection and Segmentation of Drusen in Retinal Optical Coherence Tomography Images, Ophthalmic Technologies XVIII, Proc. of SPIE vol. 6844, 2008, U.S.

Ferguson, R. Deniel et aL, Tracking Optical Coherence Tomography, Optics Letters, vol. 29, No. 18, Sep. 15, 2004.

Fernandez et al., Automated Detection of Retinal Layer Structures on Optical Coherence Tomography Images, Optics Express, vol. 13, No. 25, Dec. 12, 2005, U.S.

Final Rejection received in U.S. Appl. No. 13/353,612 dated May 10, 2017 (eleven (11) pages).

Garvin et al., Automated 3-D Intraretinal Layer Segmentation of Macular Spectral-Domain Optical Coherence Tomography Images, IEEE Transactions on Medical Imaging, vol. 28, No. 9, Sep. 2009, U.S.

Garvin, M.K., et al., Intraretinal Layer Segmentation-Search, IEEE, 0278-0062, pp. 1495-1505, 2008.

Graph cuts segmentation—medical images, Jacquot et al., I EEE,978-0-7695-3122, 2008, pp. 631-635.

Haeker et al., Automated Segmentation of Intraretinal Layers from Macular Optical Coherence Tomography Images, Society of Photo-Optical Instrumentation Engineers, 2007, U.S.

Hendargo, Hansford C. et al., Automated Non-Rigid Registration and Mosaicing for Robust Imaging of Distinct Retinal Capillary Beds Using Speckle Variance Optical Coherence Tomography, Biomedical Optics Express, vol. 4, No. 6, May 7, 2013.

International Search Report and Written Opinion issued in PCT Application No. PCT/US2016/016900 dated May 5, 2016.

International Preliminary Report on Patentability dated Jul. 23, 2013 for corresponding application PCT/US2012/021839 (filed Jan. 19, 2012).

Jung, Woonggyu et al.; "Handheld Optical Coherence Tomography Scanner for Primary Care Diagnostics" IEEE Transactions on Biomedical Engineering, vol. 58, No. 3, Mar. 2011. pp. 741-744.

International Search Report and Written Opinion dated Jan. 5, 2017 from International Application No. PCT/US16/51360.

International Search Report and Written Opinion dated May 19, 2016 from related International Application No. PCT/US16/16830.

Intra-retinal segmentation—images, Mishra et al., Optic Express 23719, Published Dec. 11, 2009, pp. 1-10.

Ishikawa et al., Macular Segmentation with Optical Coherence Tomography, Investigative Ophthalmology & Visual Science, vol. 46, No. 6, Association for Research in Vision and Ophthalmology, Jun. 2005, U.S.

Jaquot, J.Z., et al.,Graph Cuts Segmentation-Medical Images, IEEE, pp. 631-635. 2008.

Ji, NA et al., Adaptive Optics Via Pupil Segmentation for High-Resolution Imaging in Biological Tissues, Nature Methods, vol. 7, No. 2, Feb. 2010.

Kavraki, Lydia E. et al.; "Probabilistic Roadmaps for Path Planning in High-Dimensional Configuration Spaces" IEEE Transactions on Robotics and Automation, vol. 12, No. 4, Aug. 1996.

Koreeda, Y. et al.; "Development and testing of an endoscopic pseudo-viewpoint alternating system" Int J CARS, Jun. 21, 2014.

(56) References Cited

OTHER PUBLICATIONS

Kozak, Igor et al.; "Virtual reality simulator for vitreoretinal surgery using integrated OCT data" Clinical Ophthalmology 2014:8 pp. 669-672.

Larocca et al., "Optimization of confocal scanning laser opthalmoscope design." Journal of Biomedical Optics. Jul. 2013 {Jul. 20, 2013). pp. 076015-1-076015-2, 076015-8 [online].

LaRocca, Francesco et al.; "Handheld simultaneous scanning laser ophthalmoscopy and optical coherence tomography system" Biomedical Optics Express, Nov. 1, 2013 I vol. 4, No. 11, pp. 2307-2321.

LaValle, Steven M. et al.; "Rapidly-Exploring Random Trees: A New Tool for Path Planning" Department of Computer Science, Iowa State University.

Lee, K., et al. Segmentation of the Optic Disc in 3-D OCT Scans of the Optic Nerve Head. IEEE Transactions on Imaging, vol. 29(1): pp. 159-168, Jan. 2010.

Liao, Wen-Hung et al., Robust Pupil Detection for Gaze-Based User Interface, EGIHMI, Feb. 7, 2010.

Kelly, John P. et al.; "Imaging a Child's Fundus Without Dilation Using a Handheld Confocal Scanning Laser Ophthalmoscope" Arch Ophthalmol/vol. 121, Mar. 2003, pp. 391-396.

Lu et al., Automated Layer Segmentation of Optical Coherence Tomography Images, IEEE Transactions on Biomedical Engineering, vol. 57, No. 10, Oct. 2010, U.S.

Lu, Chen D.; "Handheld ultrahigh speed swept source optical coherence tomography instrument using a MEMS scanning mirror" Biomedical Optics Express, Jan. 1, 2014 I vol. 5, No. 1, pp. 293-311.

Lujan, Brandon J., et al., Revealing Henle's Fiber Layer Using Spectral Domain Optical Coherence Tomography, Investigative Ophthalmology & Visual Science, Mar. 2011, vol. 52, No. 3, 2011.

Martinez-Conde, Susan et al., The Role of Fixational Eye Movements in Visual Perception, Nature Reviews, Neuroscience, vol. 5, pp. 229-240, Mar. 2004.

McNabb, Ryan P_ et al., Distributed Scanning Volumetric SDOCT for Motion Corrected Corneal Biometry, Biomedical Optics Express, vol. 3, No. 9, Aug. 10, 2012.

Scott, Adrienne W. et al.; "Imaging the Infant Retina with a Hand-held Spectral-Domain Optical Coherence Tomography Device" Infant Retina Imaging by Hand-Held SD OCT, vol. 147, No. 2, pp. 364-373.

Mishra, A., et al., Intra-Retinal Segmentatioin-Images, Optic Express 23719, pp. 1-10, Dec. 11, 2009.

Thevenaz, Philippe et al.; "User-Friendly Semiautomated Assembly of Accurate Image Mosaics in Microscopy" Microscopy Research and Technique vol. 70: pp. 135-146 (2007).

Niemeijer et al., Vessel Segmentation in 3D Spectral OCT Scans of the Retina, Medical Imaging 2008, Image Processing, Proc. of SPIE, vol. 6914, 2008, U.S.

Non-Final Office Action received in U.S. Appl. No. 13/010,448 dated Jan. 2, 2014.

Notice of Allowance received in U.S. Appl. No. 13/010,448 dated May 13, 2014.

Larocca et al., "Optimization of confocal scanning laser opthalmoscope design." Journal of Biomedical Optics. Jul. 2013 (Jul. 20, 2013). pp. 076015-1-076015-2, 076015-8 [online] <URL: http://biomedicaloptics.spiedigitallibrary.org/article.aspx?articleid=1714879>.

Notice of Allowance received in U.S. Appl. No. 14/337,215 dated Dec. 23, 2015.

Notice of Allowance received in U.S. Appl. No. 15/049,103 dated Oct. 10, 2016.

Office Action received in U.S. Appl. No. 14/337,215 dated May 12, 2015.

Office Action received in U.S. Appl. No. 14/337,215 dated Nov. 5, 2014.

Office Action received in U.S. Appl. No. 15/049,103 dated Jul. 5, 2016.

Otsu, A Threshold Selection Method from Gray-Level Histograms, IEEE Transactions on Systems, Man, and Cybernetics, vol. SMC-9, No. 1, Jan. 1979, U.S.

PCT International Search Report for PCT International Application No. PCT/US15/13870.

PCT International Written Opinion for PCT International Application No. PCT/US15/13870.

PCT Preliminary Report on Patentability and Written Opinion dated May 8, 2014 for related PCT International Application No. PCT/US2014/013243.

PCT Search Report and Written Opinion dated Jul. 13, 2012 for related application PCT/US2012/021839; dated Jan. 19, 2012.

Perstein, M., Algorithms, Control Data Corp., Palo Alto, California.

Pircher, Michael et al., Simultaneous SLO/OCT Imaging of the Human Retina with Axial Eye Motion Correction, Optics Express, vol. 15, No. 25, Dec. 4, 2007.

Related application PCT/US2012/021839 filed Jan. 19, 2012 entitled System Enhancements for Ophthalmic Surgical Microscope Mounted Optical Coherence Tomography, not yet published.

Schulze, Jürgen P. et al.; "Visualization of Three-Dimensional Ultra-High Resolution OCT in Virtual Reality" Ophthalmology Department, Lariboisiére Hospital, APHP, Paris, France.

SDI/BIOM: Still the Standard in Wide-Angle Viewing for All Microscope Models!, Insight Instruments, Inc., Stuart, Florida.

Shen, Liangbo et al.; "Novel Microscope-Integrated Stereoscopic Heads-up Display for Intrasurgical OCT in Ophthalmic Surgery", The Association for Research in Vision and Ophthalmology; Jun. 2015, vol. 56, 3514.

Shi et al., Normalized Cuts and Image Segmentation, IEEE Transactions on Pattern Analysis and Machine Intelligence, vol. 22, No. 8, Aug. 2000, U.S.

Shi, Minyan et al.; "A Stereo-Fluoroscopic Image-Guided Robotic Biopsy Scheme" IEEE Transactions on Control Systems Technology, vol. 10, No. 3, May 2002, pp. 309-317.

Stephanie J. Chiu, Cynthia A. Toth, Catherine Bowes Rickman, Joseph A. Izatt, and Sina Farsiu, "Automatic Segmentation of Cloaed-contour Features in Ophthalmic Images Using Graph Theory and Dynamic Programming", Published Apr. 26, 2012, Optical Society of America.

Takeda et al., Kernel Regression for Image Processing and Reconstruction, IEEE Transactions on Image Processing, vol. 16, No. 2, Feb. 2007, U.S.

The Age-Related Eye Disease Study Research Group, The Age-Related Eye Disease Study System for Classifying Age-Related Macular Degeneration From Stereoscopic Color Fundus Photographs: The Age-Related Eye Disease Study Report No. 6, Elsevier Service Inc., vol. 132, No. 5, 2001, U.S.

Tolliver et al., Unassisted Segmentation of Multiple Retinal Layers via Spectral Rounding, Presented in ARVO 2008 Annual Meeting, Fort Lauderdale, Florida, U.S., Apr. 2008.

U.S. Final Office Action for U.S. Appl. No. 14/337,215, dated May 12, 2015.

U.S. Non-Final Office Action for U.S. Appl. No. 13/010,448, dated Jan. 2, 2014.

U.S. Non-Final Office Action for U.S. Appl. No. 14/337,215, dated Nov. 5, 2014.

U.S. Non-Final Office Action for U.S. Appl. No. 15/049,103, dated Jul. 5, 2016.

U.S. Notice of Allowance for U.S. Appl. No. 1301448, dated May 13, 2013.

U.S. Notice of Allowance for U.S. Appl. No. 14/337,215, dated Jan. 11, 2016.

U.S. Notice of Allowance for U.S. Appl. No. 15/049,103, dated Oct. 24, 2016.

U.S. Office Action Response to Non-Final Office Action for U.S. Appl. No. 14/337,215, dated Apr. 6, 2015.

U.S. Office Action Response to Non-Final Office Action for U.S. Appl. No. 15/049,103, dated Oct. 6, 2016.

U.S. Response to Non-Final Office Action for U.S. Appl. No. 13/010,448, dated Mar. 31, 2014.

Viehland, Christian et al.; "Enhanced volumetric visualization for real time 4D intraoperative ophthalmic swept-source OCT" Biomedical Optics Express 1815, May 1, 2016 I vol. 7, No. 5 I.

Warshall, A Theorem on Boolean Matrices, Computer Associates, Inc., Woburn, Massachusetts, U.S.

(56) References Cited

OTHER PUBLICATIONS

Wieser, Wolfgang et al., Multi-Megahertz OCT: High Quality 3D Imaging at 20 Million A-Scans and 4_5 GVoxels Per Second, Optics Express, vol. 18, No. 14, Jun. 30, 2010.
Witte, S., Plaw;;ka, A., Ridder, M. C., van Berge, L., Mansvelder, H. D., & Groot, M. L. (2012). Short-coherence off-axis-holographic phase microscopy of live cell dynamics. Biomedical Optics Express, 3(9), 2184-2189. http://doi.org/10.1364/BOE.3.002184.
Yazdanpanah et al., Segmentation of Intra-Retinal Layers from Optical Coherence Tomography Images Using an Active Contour Approach, IEEE, 2010, U.S.
International Preliminary Report on Patentability for Application No. PCT/US2016/016900 dated Aug. 8, 2017.
Final Office Action issued in counterpart U.S. Appl. No. 15/547,537 dated Oct. 25, 2018 (six (6) pages).
Notice of Allowance issued in counterpart U.S. Appl. No. 15/547,537 dated Jan. 2, 2019 (seven (7) pages).

COMPACT TELESCOPE CONFIGURATIONS FOR LIGHT SCANNING SYSTEMS AND METHODS OF USING THE SAME

CROSS REFERENCE TO RELATED APPLICATION

This is a 371 national stage patent application, which claims priority to PCT International Patent Application No. PCT/US2016/016900, filed Feb. 5, 2016, and titled COMPACT TELESCOPE CONFIGURATIONS FOR LIGHT SCANNING SYSTEMS AND METHODS OF USING THE SAME, which claims the benefit of U.S. Provisional Patent Application No. 62/112,389, filed Feb. 5, 2015 and titled COMPACT TELESCOPE DESIGN FOR LIGHT SCANNING SYSTEMS AND METHODS OF USING THE SAME; the disclosures of which are incorporated herein by reference in their entireties.

FEDERALLY SPONSORED RESEARCH OR DEVELOPMENT

The technology disclosed herein was made in part with government support under Federal Grant Nos. EY021321 and EY023039 awarded by the National Institutes of Health (NIH). The United States government has certain rights in the technology.

TECHNICAL FIELD

The present subject matter relates to light scanning systems. More particularly, the present subject matter relates to compact telescope configurations for light scanning systems and methods of using the same.

BACKGROUND

Scanning laser ophthalmoscopy (SLO) and optical coherence tomography (OCT) are widely used retinal imaging modalities that can assist in the diagnosis of retinal pathologies. SLO is a confocal imaging technique that produces real-time, high contrast 2-D en-face retinal images by raster scanning illumination and detecting backscattered light through a pinhole. OCT, like SLO, utilizes raster scanning and confocal detection but also employs coherence gating in the axial direction, which allows for high resolution depth sectioning. Current-generation clinical spectral domain OCT (SD-OCT) and swept source (SS-OCT) systems utilize rapid acquisition along the depth axis (depth-priority scanning) at 20-100 kHz line rates to produce high-resolution 2-D cross-sectional images (B-scans) near video rate.

The combination of SLO and OCT has been explored by various groups in either simultaneous or sequential SLO-OCT imaging. Some of these imaging systems have been translated to the clinic as table-top systems mounted to a patient positioning frame like those used in modern slit-lamps. However, due to the physical size and design of these tabletop systems, imaging is limited to patients who are able to sit in an upright position and fixate for several minutes. A portable, handheld SLO-OCT probe would be useful in acquiring motion-corrected OCT volumes in young children, as well as patients that are supine, under anesthesia, or otherwise unable to maintain the required posture and fixation. While compact or handheld SLO systems and handheld OCT systems have been described, there is a need for improved systems that have a more compact and lightweight design.

Conventional telescopes, such as Galilean and Keplerian telescopes, require two sets of optical elements with a spacing between them equal to the sum of their effective focal lengths. This spacing can contribute to a significant fraction of the telescope size especially for large magnifications and long focal lengths. Although reducing the focal lengths of the optics used in the telescope by a constant factor can be done to reduce telescope size while preserving magnification, practical constraints such as the minimum working distance from a light scanner to the telescope pose fundamental limits to the extent to which the focal lengths of telescope optics can be decreased. Handheld light scanning systems employing telescopes for retinal imaging purposes have been demonstrated. In such cases, a collimated beam was used prior to a light scanner and a conventional Keplerian telescope was utilized to relay an image of the scanners to the pupil plane of the eye. However, such designs require a spacing equal to the sum of the effective focal lengths of the telescope's optical elements and therefore limit the minimum size of handheld light scanning systems. For at least this reason, there is a desire to provide for smaller handheld designs for systems utilizing both a light scanner and a telescope that relays an image of the light scanner.

SUMMARY

Disclosed herein are compact telescope configurations for light scanning systems and related methods. In accordance with an aspect, systems disclosed herein use a converging beam prior to a light scanner to minimize the separation between telescope optics. Field correcting optics can be used to compensate for optical aberrations introduced by this technique while producing a collimated beam output. The presently disclosed subject matter can be used to maintain telescope magnification while further reducing the telescope size in light scanning systems. Techniques and systems disclosed herein can be used to provide small handheld designs for systems using both a light scanner and a telescope that relays an image of the light scanner.

According to an aspect, a system for imaging or relaying an image of an object includes a first optical element having a first focal length $f_1$ for imaging or relaying an image of an object at the distance $f_1$ from the first optical element. The system also includes a second optical element having a second focal length $f_2$ and having an optical axis substantially aligned with an optical axis of the first optical element for receiving an image of the object from the first optical element and for focusing an output of the image at the distance $f_2$ from the second optical element on a side that opposes the first optical element. The first optical element and the second optical element are separated by a distance of about $$f_1 + f_2 - \frac{f_1^2}{r},$$

wherein r is the finite radius of curvature of the wavefront of light located at the object or image of the object.

BRIEF DESCRIPTION OF THE DRAWINGS

The foregoing aspects and other features of the present subject matter are explained in the following description, taken in connection with the accompanying drawings, wherein.

DETAILED DESCRIPTION

Figure 1:
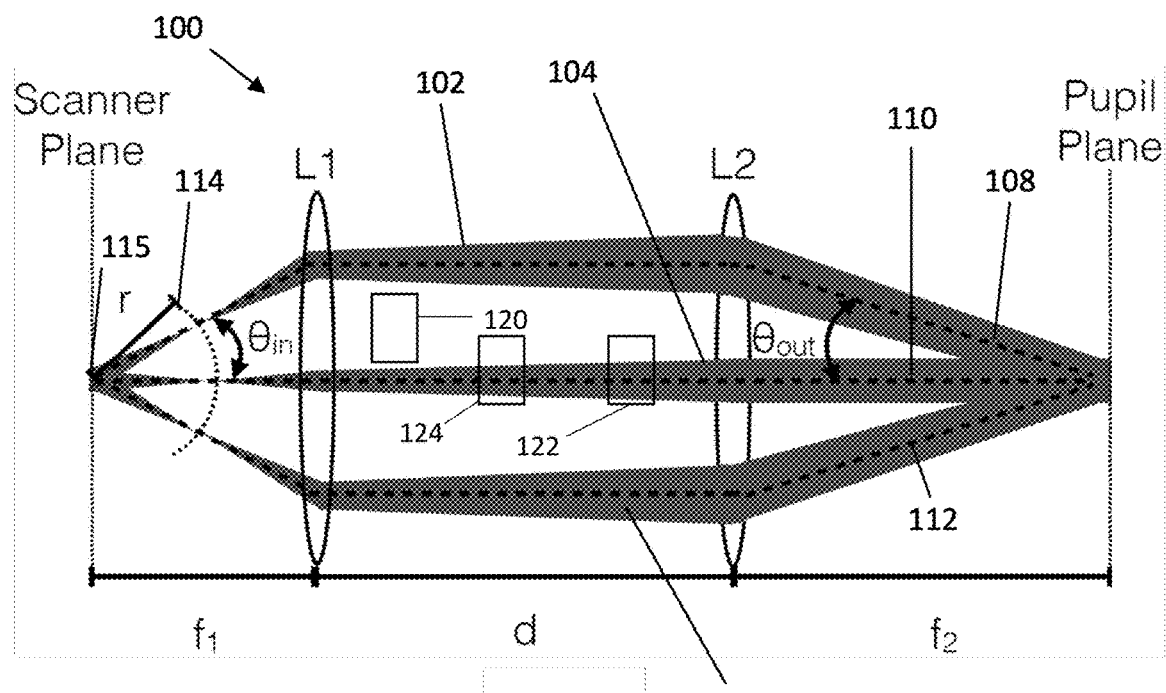
FIG. 1 is a diagram of an example converging-at-scanner telescope in accordance with embodiments of the present disclosure.

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "about" is understood as within a range of normal tolerance in the art, for example within 2 standard deviations of the mean. The term "about" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

Unless otherwise defined, all technical terms used herein have the same meaning as commonly understood by one of ordinary skill in the art to which this disclosure belongs.

In accordance with embodiments of the disclosed subject matter, compact light scanning systems are provided that utilize a converging beam prior to the scanner to minimize the empty space within the telescope and field correcting optics to compensate for optical aberrations. In accordance with embodiments, the systems can be used as part of a combined scanning laser ophthalmoscopy and optical coherence tomography handheld probe. As a result of the presently disclosed subject matter, the size of telescopes in light scanning systems can be significantly reduced by minimizing the empty space within the telescope and correcting for the resulting error optically both before and after the light scanner.

Systems and methods disclosed herein may be used in, for example, bar scanners, laser printers, endoscopes, confocal microscopes, SLO, OCT systems, and other devices that utilize both telescopes or beam expanders and light scanning. This compact design in a light scanner can be important for reducing the size of such equipment. These compact designs can facilitate better portability and increased comfort for the operator.

Compact telescope design can be especially important for retinal imaging modalities, such as SLO and OCT, when developing handheld probe designs. Because of limitations in the aperture size of current high-speed 2D scanning mirrors, large magnifications are often necessary to optimize the imaging resolution at the retina. Some traditional methods of reducing telescope size while preserving magnification require reducing the focal lengths of the optics used in the telescope by a constant factor. However, practical constraints such as the minimum working distance from the light scanner to the telescope and from the telescope to the eye can pose fundamental limits to the extent to which the focal lengths of the telescope optics can be decreased. The presently disclosed subject matter can be used to further reduce the telescope size beyond that possible by simply reducing the focal lengths of the telescope optics. Further, the presently disclosed subject matter can also be applied to any suitable telescope between two light scanners that serve to image one scanner on to the other.

As referred to herein, an "optical element" may be any suitable component for manipulating light. For example, an optical element may be a lens. In other examples, a refractive optical element may include dioptrics, catoptrics, catadioptrics, diffractive optics, the like and any combination thereof. Also, it should be understood that when a particular optical element (e.g., a lens) is referred to herein, then any other suitable one or more optical elements may replace the particular optical element for achieving the same function as will be understood by those of skill in the art.

As referred to herein, a "light scanner" may be any suitable component for scanning light. For example, a scanner may be a 2D microelectromechanical system (MEMS) scanner. In other examples, a light scanner may be a galvanometric scanner, resonant scanner, reflective polygon scanner, rotating prism scanner, optical phased array, the like, or any combination thereof. Also, it should be understood that when a particular light scanner (e.g., a MEMS scanner) is referred to herein, then any other suitable one or more light scanners may replace the particular optical element for achieving the same function as will be understood by those of skill in the art.

FIG. 1 illustrates a diagram of an example converging-at-scanner telescope 100 in accordance with embodiments of the present disclosure. Relevant lengths and angles are labeled in the figure. Shaded areas 102, 104, and 106 denote scan angles. Chief rays are denoted by dashed lines 108, 110, and 112. Dotted circle 114 indicates the location of beam convergences from light with a radius of curvature r at the light scanner in the case that r is less than $f_1$. Here, a positive value of r refers to a radius of curvature that would result in a converging beam after the light scanner while a negative value of r would result in a diverging beam after the light scanner. A general schematic of the converging-at-scanner telescope design is shown in FIG. 1. The beam enters the telescope converging at a distance r from a position 115 for the scanner. There are two lenses, L1 and L2, with focal lengths $f_1$ and $f_2$, respectively. The layout is identical to a traditional 4f imaging telescope, except the distance between the lenses d, which is decreased to compensate for the initial defocus caused by the converging beam. As r is increased to infinity, the input beam becomes collimated and d becomes $f_1+f_2$ as in a 4f telescope. Because the chief rays of the scan all start a lateral distance $f_1$ from the principal plane of L1, they travel in infinity space between the lenses, and thus converge at a lateral distance $f_2$ after the principal plane of L2. Additionally, the same lateral and angular magnifications based on the length of the lenses apply as for a 4f telescope ($f_2/f_1$ and $f_1/f_2$ respectively). Thus, a 4f imaging configuration is easily converted to a converging-at-scanner design without change in angular range or spot size. In the limiting case where d=0, the two optical elements can be combined into a single element with focal length $$f' = \frac{f_1 f_2}{f_1 + f_2}.$$

In this case, $$r = \frac{f_1^2}{f_1 + f_2}.$$

By approximating L1 and L2 as thin, paraxial lenses, the following expression for the total length of the telescope $l$ can be derived:

$$\ell = f_1 + f_2 + d$$
$$= f_1 + f_2 + \left(f_1 + f_2 - \frac{f_1^2}{r}\right)$$

Figure 2:
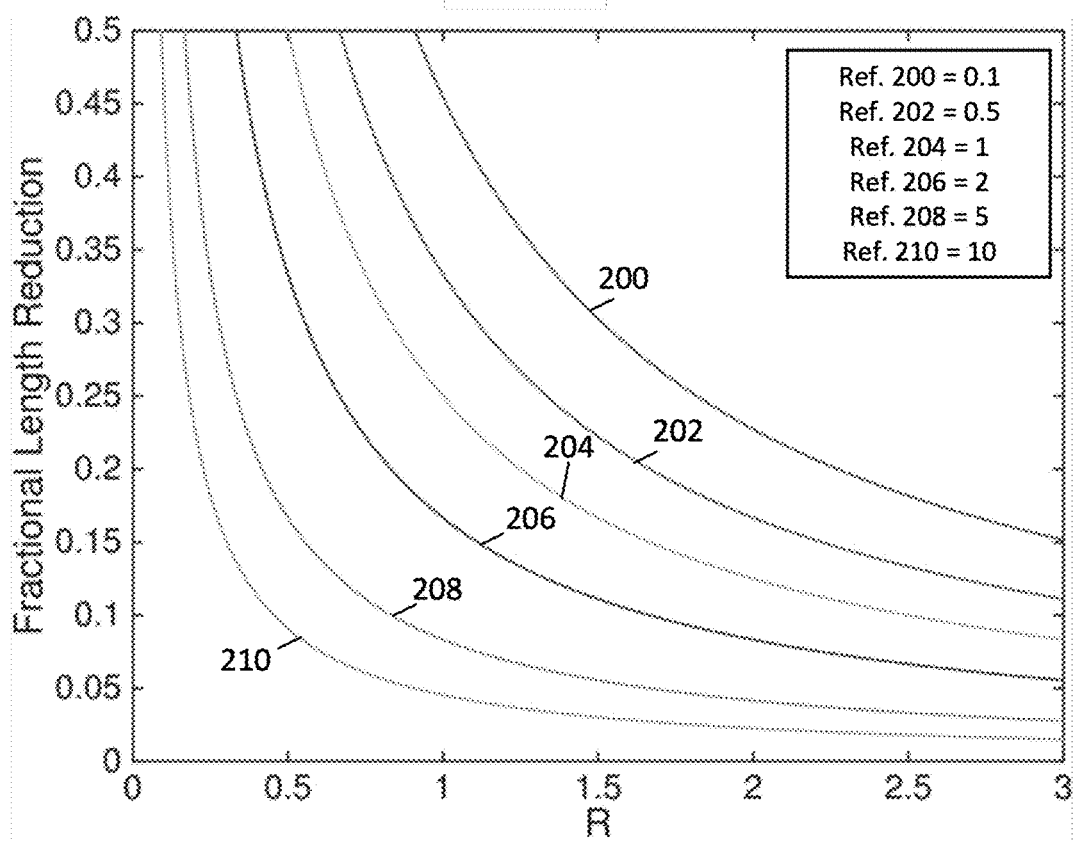
FIG. 2 is a plot of the fractional length reduction of the converging-at-scanner telescope versus the normalized radius of curvature R of the wavefront of light at the light scanner for several values of telescope magnifications M.

By normalizing this expression by the total length of a 4f telescope, $2f_1+2f_2$, a general expression for the fractional length of the telescope, L, can be derived:

$$L = 1 - \frac{1}{2R(1+M)}$$

where $R=r/f_1$ (normalized radius of curvature) and $M=f_2/f_1$ (lateral magnification of the telescope). A plot of the latter term in this equation, the fractional reduction in telescope length, is shown in FIG. 2, which illustrates a plot of the fractional length reduction of the converging-at-scanner telescope versus the normalized radius of curvature R of the wavefront of light at the light scanner for several values of telescope magnifications M.

However, if purely paraxial lenses are used, a small value of r induces a high field curvature. In the previous work, the field curvature was induced intentionally, but for many imaging systems field curvature is undesirable as it leads to regions of the image being out of focus. To quantify the degradation of the image, consider a Gaussian input beam of diameter D. The beam can converge after a distance r, giving it a divergence angle $\phi$ of $$\phi = \operatorname{atan}\left(\frac{D}{2r}\right)$$

and therefore a Rayleigh range of $$z_R = \frac{4\lambda}{\pi\phi^2} = \frac{4\lambda}{\pi \operatorname{atan}^2\left(\frac{D}{2r}\right)}$$

The image can be said to be out of focus if the beam is scanned to an angle $\theta_{max}$ such that the focus of the scanned beam is a Rayleigh range away from the focus of the unscanned beam. The expression for $\theta_{max}$ is:

$$\theta_{max} = \operatorname{acos}\left(1 - \frac{z_R}{r}\right)$$

Figure 3:
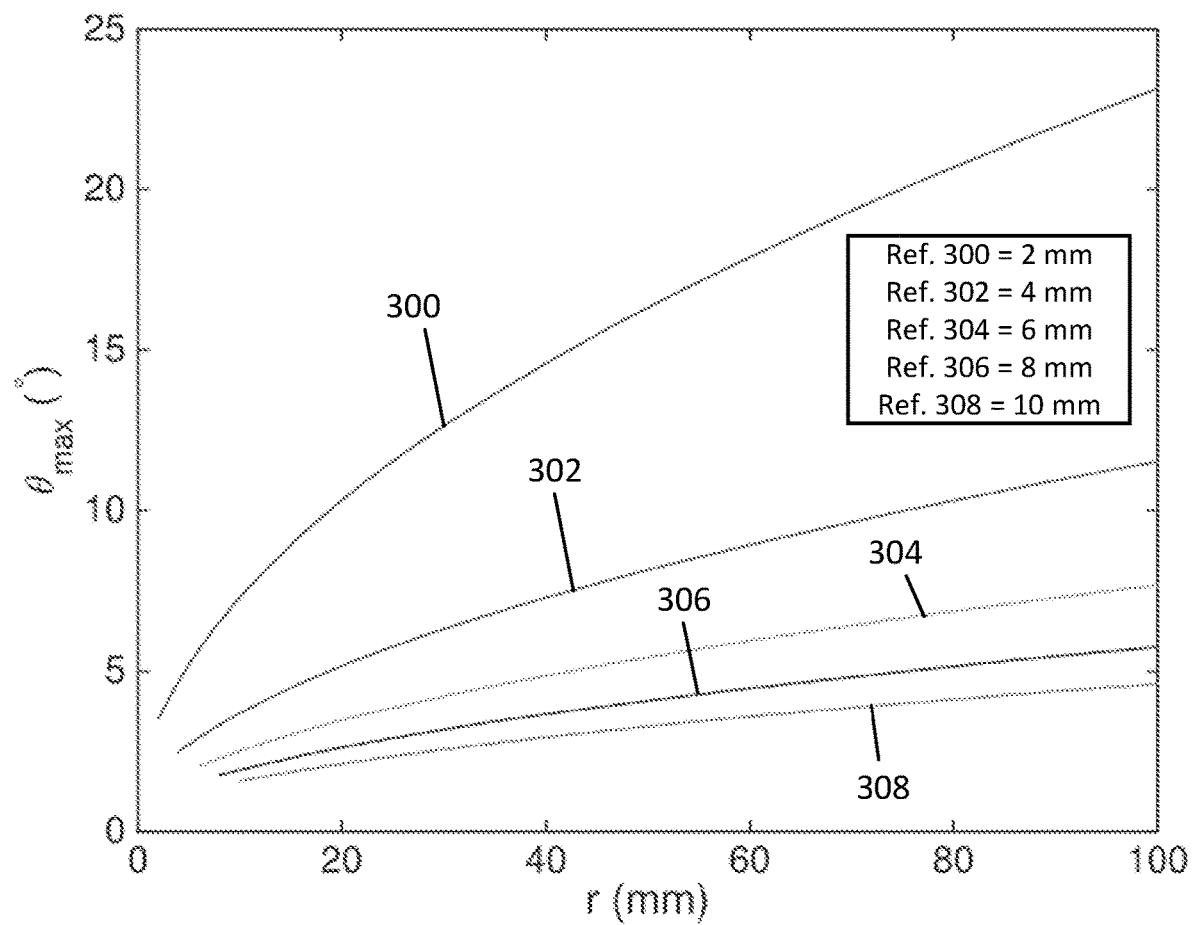
FIG. 3 is a plot of the maximum scan angle of the light scanner $\theta_{max}$ versus the radius of curvature r of the wavefront of light at the light scanner for a variety of input beam diameters D.

A plot of $\theta_{max}$ versus r for a variety of input beam diameters is shown in FIG. 3. The plots demonstrate that a short r length greatly reduces the potential in-focus scan angle range. It should be noted that even at one Rayleigh range, the spot size is increased by a factor of $\sqrt{2}$ which may still lead to blurring.

If the application calls for a scan angle greater than $\theta_{max}$ or the scan is within $\theta_{max}$ but the blur at the edges of the image is too great, additional optics can be introduced to reduce the field curvature. One method for reducing field curvature is to simply introduce a zero-power field flattening lens into the system. If $r<f_1$, there can be a focal plane between the scanner and L1; otherwise, there can be a focal plane between L1 and L2. Typically, the field flattener (an example location of which is represented by box 120 in FIG. 1) may be placed as close to the focal plane as possible to minimize the induced aberrations, but the field flattener may be placed in any suitable position within the system. As an example, one meniscus (represented by box 122) and two biconvex lenses (represented by box 124) may be positioned between lenses L1 and L2, and have an optical axis substantially aligned with the optical axes of the lenses L1 and L2.

A second method to remove field curvature may be to design custom optics for L1 that incorporate focusing power, aberration correction, and field flattening in a low number of elements. Although custom optics are a more expensive option, this approach will result in the lowest total amount of aberration (including field curvature).

Figure 4:
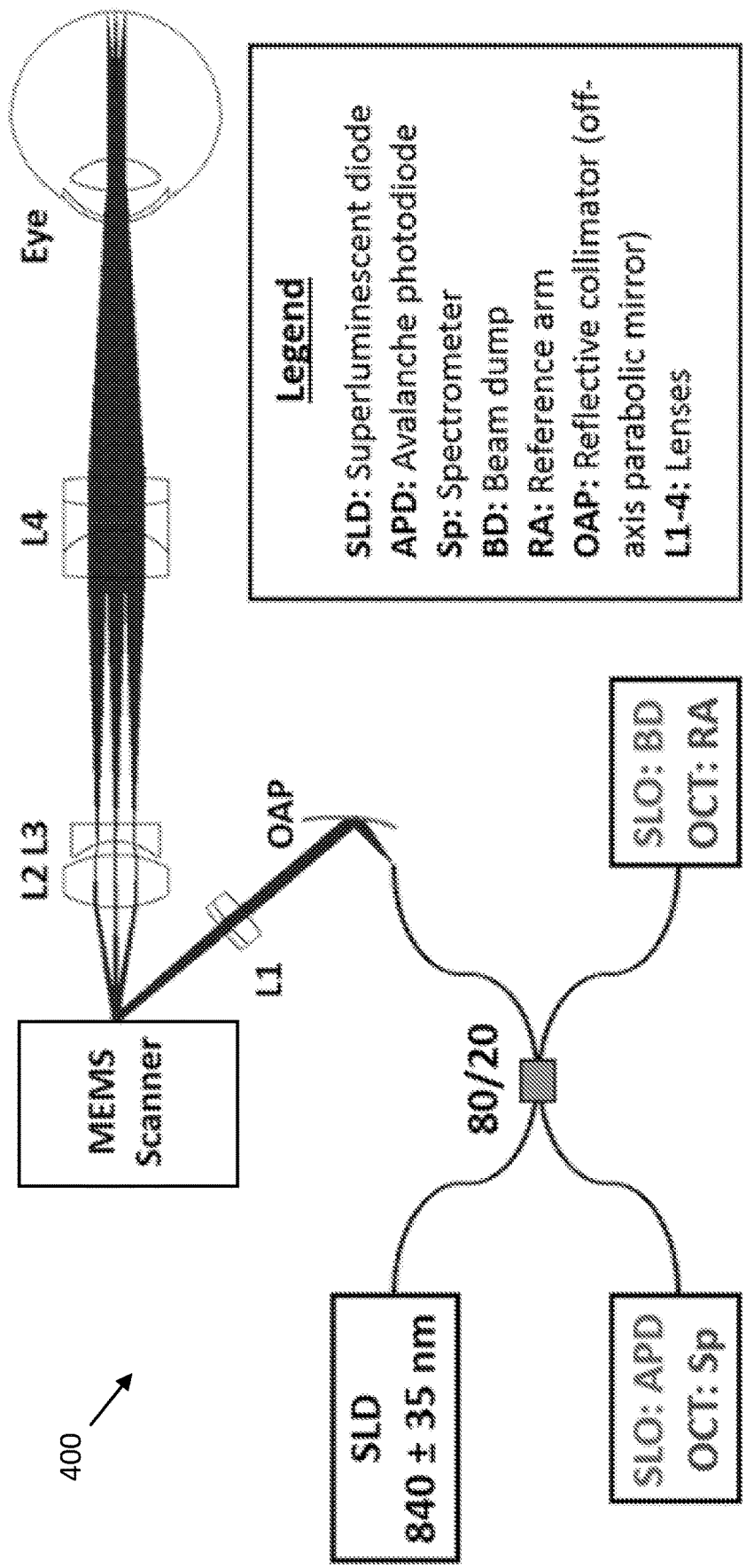
FIG. 4 is a schematic diagram of an SLO-OCT handheld probe and optical system in accordance with embodiments of the present disclosure.
Figure 5:
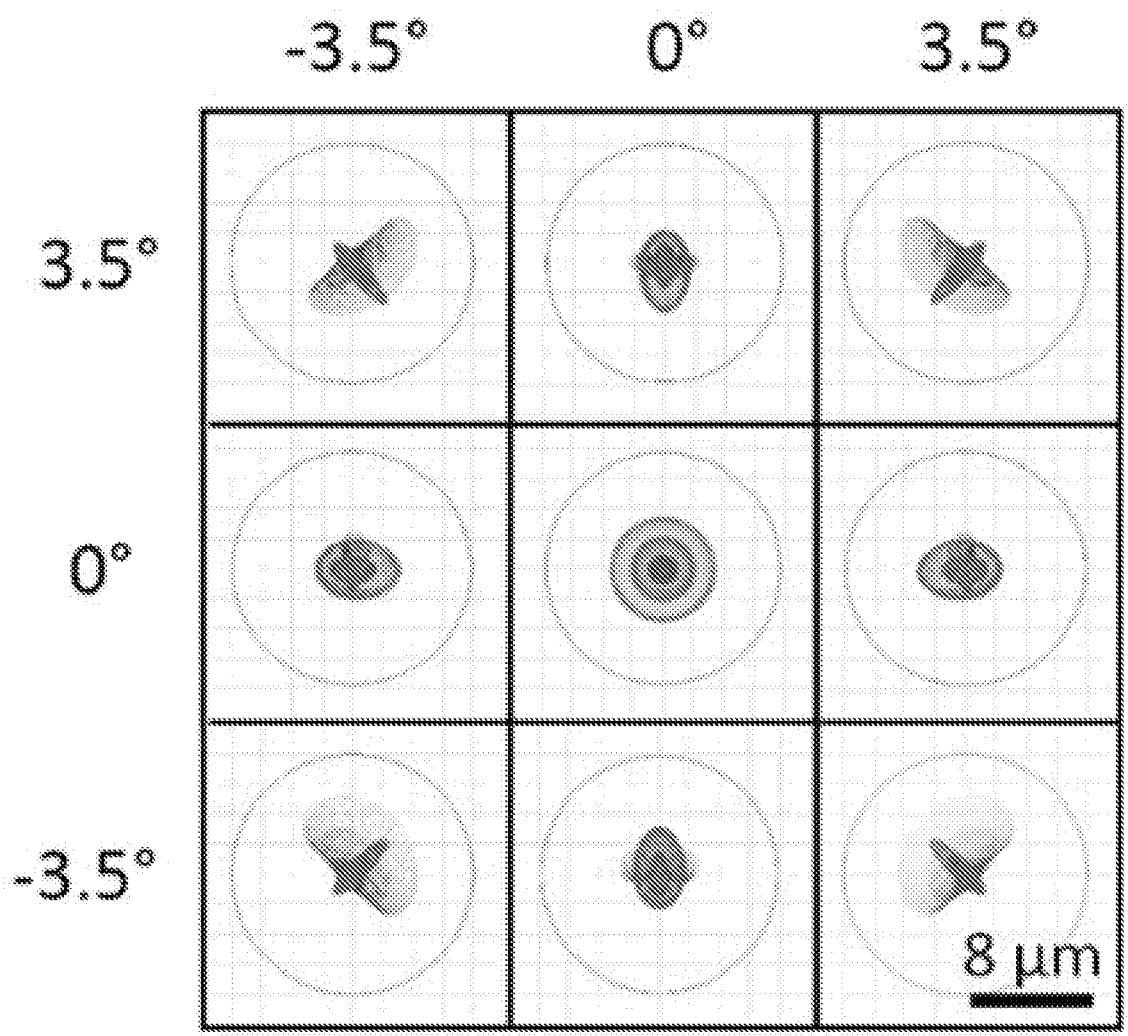
FIG. 5 depicts spot diagrams (grayscaled for 3 wavelengths spanning 805-870 nm) from the probe shown in FIG. 4 for both SLO and OCT illumination on the retina of a model eye spanning a 7° FOV.

A compact telescope design in accordance with embodiments disclosed herein may be used to prototype an SLO and OCT handheld probe. For example, FIG. 4 illustrates a schematic diagram of an SLO-OCT handheld probe and optical system 400 in accordance with embodiments of the present disclosure. Referring to FIG. 4, the optical components of the system 400 are labeled and described in the legend. The system may be used to image in SLO mode or OCT mode. For both SLO and OCT imaging, light from an 840±35 nm superluminescent diode (SLD) can be directed through an 80/20 coupler to an input fiber port on the handheld probe. Light sources with other central wavelengths or bandwidths may also be used. Also splitting ratios other than 80/20 can be employed for the coupler. Light to the handheld probe can be collimated by an off-axis parabolic mirror and then focused by a lens prior to a 1 mm aperture MEMS scanner. After the MEMS scanner is the proposed compact telescope, which includes a combination of custom (L2 and L4) and commercial (L3) lenses to magnify the beam at the scanners to create a 2.8 mm beam at the pupil of the eye with a 7° field of view (FOV). Field curvature was minimized in this design by suitable optics that incorporate focusing power, aberration correction, and field flattening in a low number of elements. Although such optics may be a more expensive option, this approach can result in the lowest total amount of aberration (including field curvature). A plano-concave lens (L3) can remove most of the field curvature and may be placed soon after the focal plane. Prior to this lens, a custom biconvex lens (L2) may be suitably positioned. In one experimental design, the positioning of lens L2 was optimized in optical design software ZEMAX (available from Zemax LLC), such that the principal plane of the L2 and L3 lens pair was a focal length away from the scanner and the remaining monochromatic aberrations of the system including residual field curvature were minimized. The last optical element of the telescope, an asymmetric triplet (L4), was optimized to provide a telescope magnification of 2.8, correct for chromatic aberrations across the illumination spectrum (840±35 nm), and minimize induced monochromatic aberrations. The resulting optical design achieved a near-diffraction limited resolution of 8 µm over a 7° FOV on a model eye as shown by the geometric spot diagrams in FIG. 5, which depicts spot diagrams (grayscaled for 3 wavelengths spanning 805-870 nm) for both SLO and OCT illumination on the retina of a model eye spanning a 7° FOV. Backscattered light from the eye was collected through the same fiber used for illumination and directed to a spectrometer when imaging in OCT mode or an avalanche photodiode when imaging in SLO mode. The remaining end of the 80/20 coupler was connected to a beam dump or a reference arm when imaging in SLO or OCT mode, respectively. Another possible collection scheme may use a dual-clad fiber as an alternative to the coupler used in this embodiment. In this scheme, the single mode core of the dual clad fiber can input light into the handheld probe while both the single mode core and multimode outer cladding could collect backscattered light used for imaging in either SLO or OCT modes.

SLO images were acquired at 14.8 frames per second (fps) with 500 lines per frame and 675 pixels per line by using a 5 MHz digitizer, applying a 3.7 kHz sinusoidal waveform to the fast axis of the MEMS scanner, and utilizing both the forward and backward sweeps of the sinusoidal scan as separate lines in the frame. For OCT imaging, B-scans were acquired at 40 fps with 500 A-scans/B-scan and 2048 pixels/A-scan, by using a 20 kHz A-scan rate (limited by the speed of the spectrometer) and a 40 Hz sawtooth waveform to the fast axis of the MEMS scanner.

Figure 6:
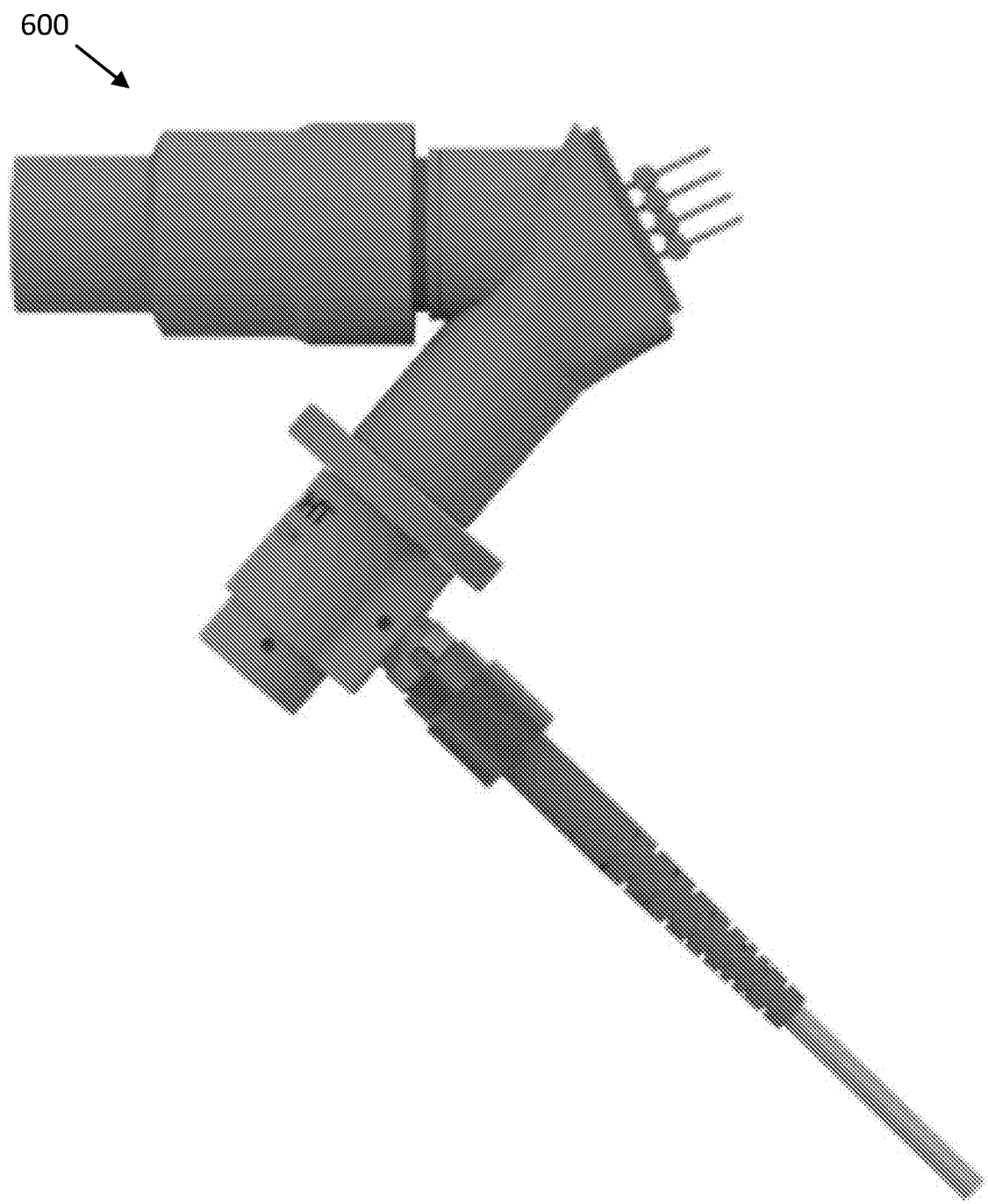
FIG. 6 is a side view of an example handheld probe in accordance with embodiments of the present disclosure.
Figure 7:
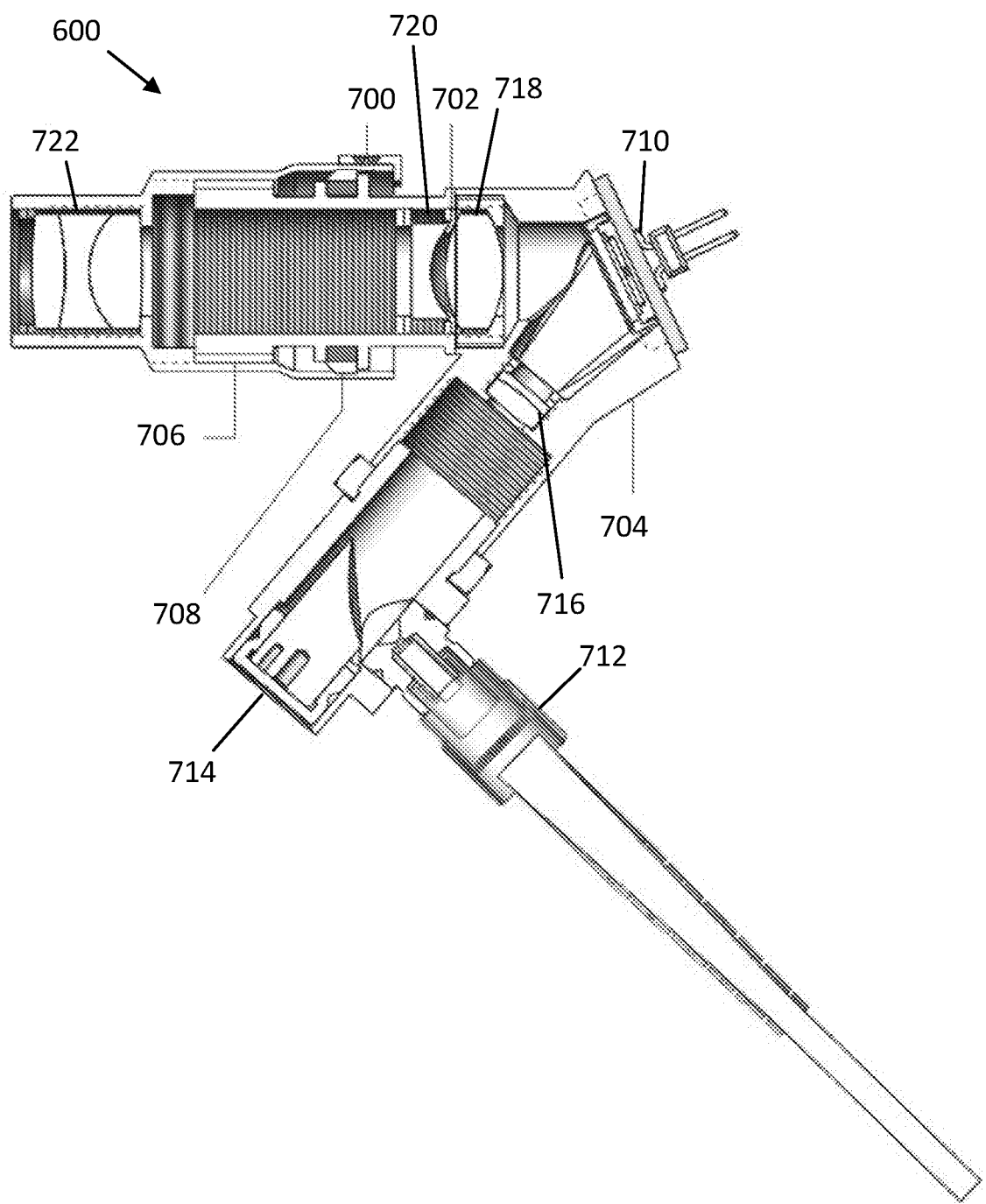
FIG. 7 is a cross-sectional side view of the example handheld probe shown in FIG. 6.
Figure 8:
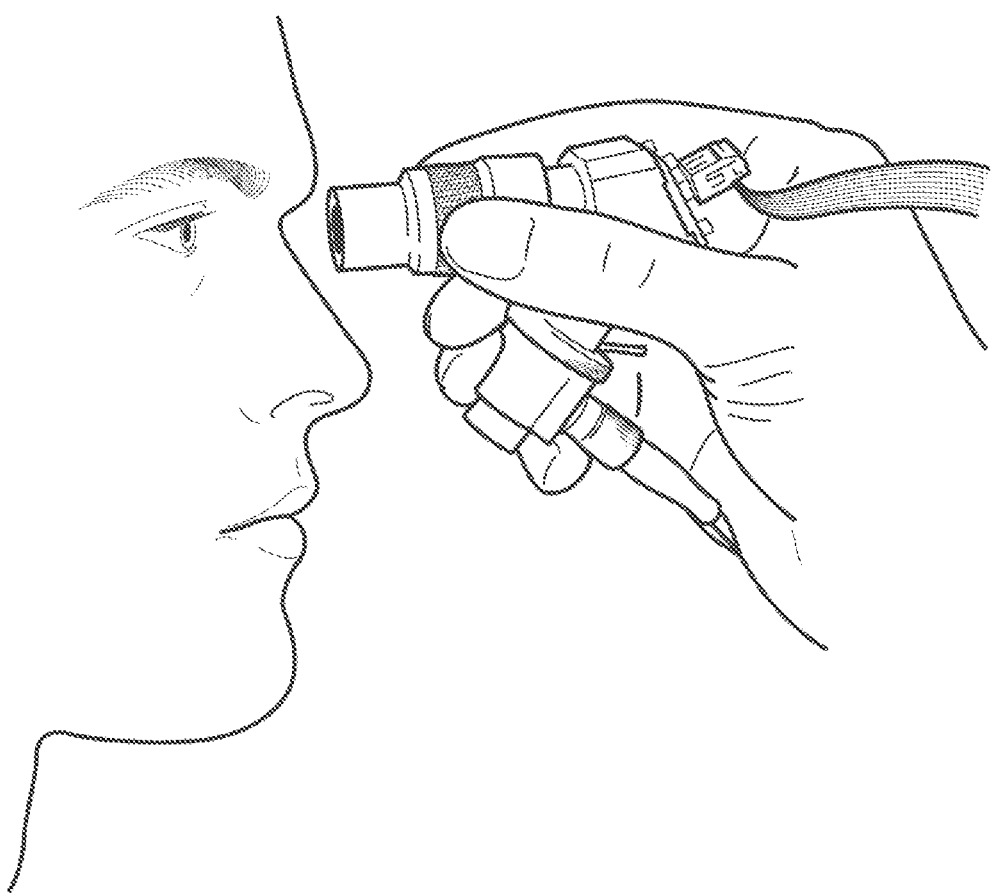
FIG. 8 is an image of the fabricated probe in handheld use for imaging a subject's eye.

FIGS. 6 and 7 illustrates different views of an example handheld probe 600 in accordance with embodiments of the present disclosure. Particularly, FIG. 6 is a side view of the probe 600, and FIG. 7 is a cross-sectional side view of the probe 600. Referring to FIG. 7, the probe 600 includes an L-shaped key 700 to prevent the outer bore from being unintentionally removed when adjusting focus. The probe 600 also includes a spacer 702 with tangential and toroidal interfaces for supporting the close proximity of the multi-scale lens pair located after the MEMS scanner while minimizing stress-induced distortions of the optical wavefront. Reference number 704 indicates the probe body, which may be made of 7075 aluminum or any other suitable material. The probe 600 includes a 4 start high lead threaded interface 706 for rapid focus adjustment. Further, the probe 600 includes a polytetrafluoroethylene radio tensioning ring 708 for preventing the objective from unintentional translation. Radial tension can be supplied by 20% compression of a neoprene foam ring. It is noted that the mechanics of the probe 600 were designed and modeled in SOLIDWORKS software, available from Dassault Systems. The probe 600 in this example has a form factor of 7×6×2.5 cm and a weight of about 94 g. The last lens of the probe was allowed to translate by rotating the probe's outer bore in order to provide ±3 D of refractive correction. FIG. 8 is an image of the fabricated probe in handheld use for imaging a subject's eye.

With continued reference to FIG. 7, the probe 600 include a MEMS scanner 710 is the MEMS scanner. Further, the probe includes an input fiber 712 to provide light to the system from the SLD. The probe 600 also includes a reflective collimator (OAP) 714 (see the example of FIG. 4). Further, the probe 600 include lens L1 716, lens L2 718, lens L3 720, and lens L4 722 (see the example of FIG. 4).

Figure 9:
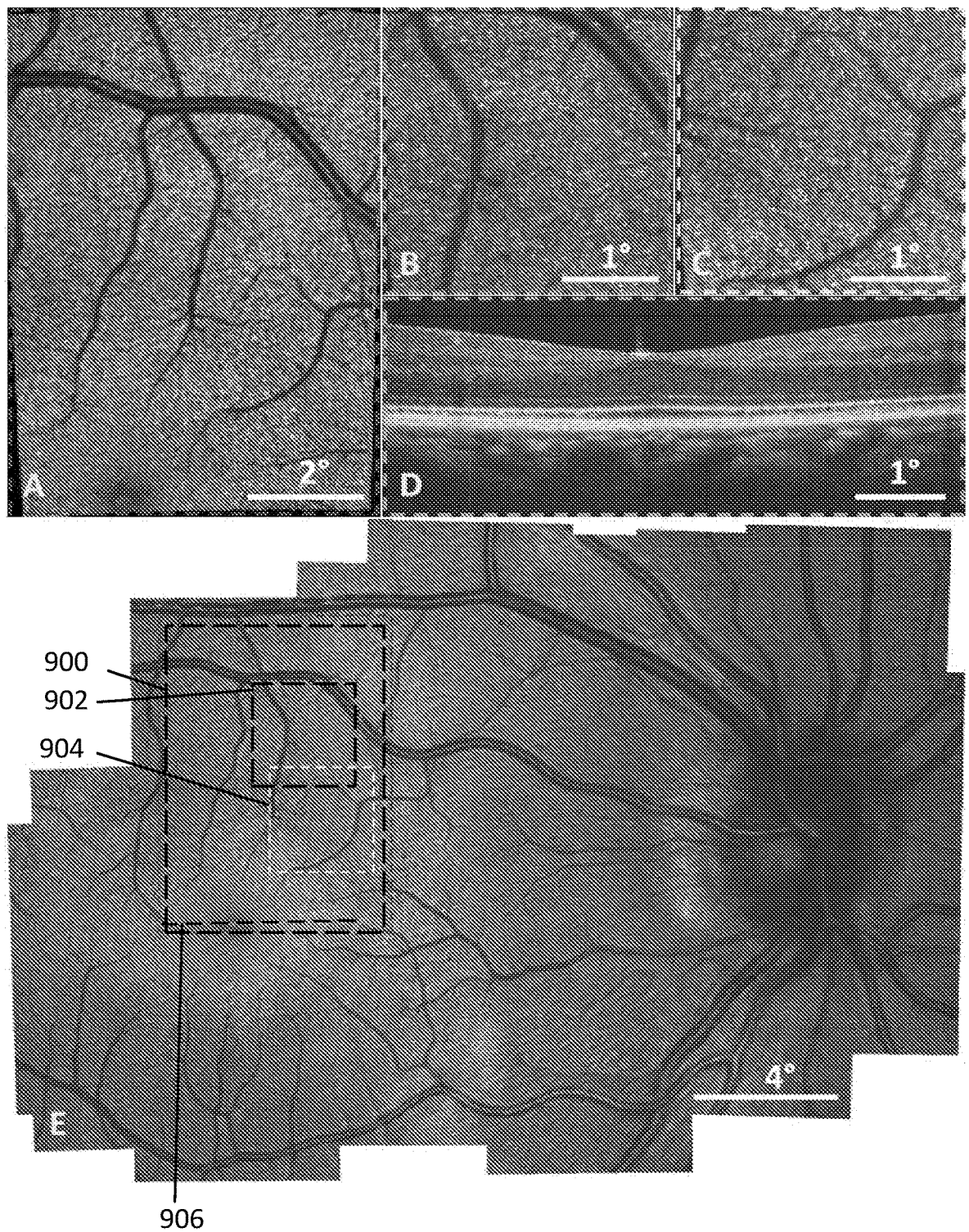
FIG. 9 are images generated by an example SLO-OCT handheld probe in accordance with embodiments of the present disclosure.
Figure 10:
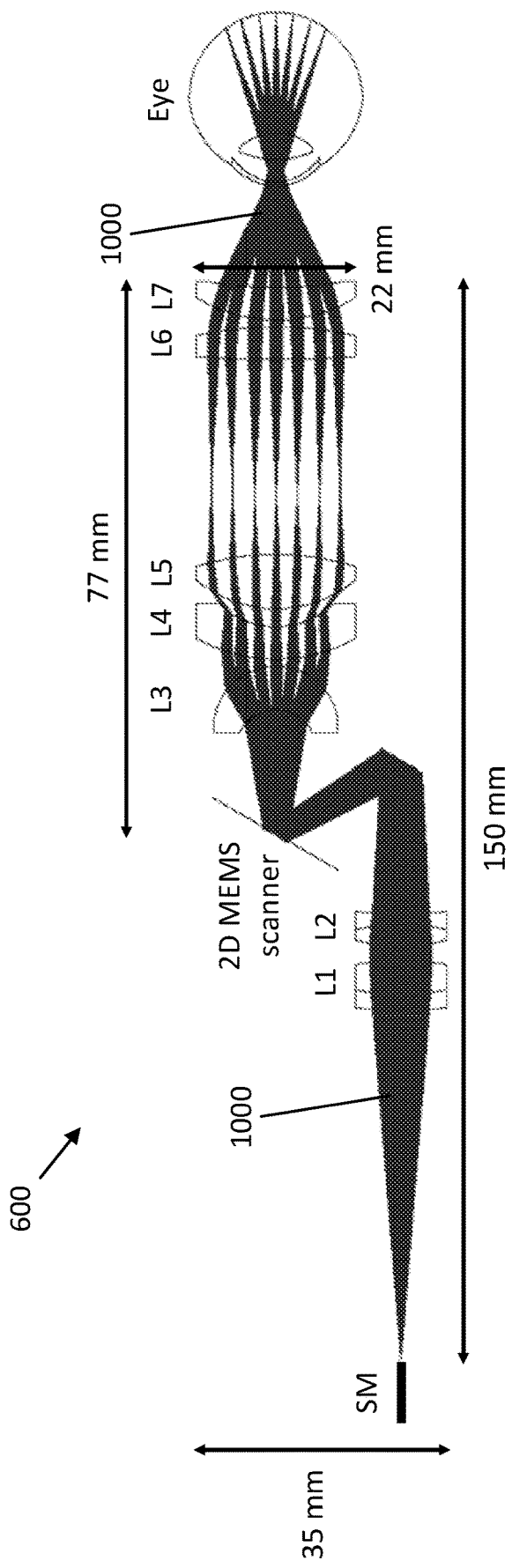
FIG. 10 is a diagram of another example probe in accordance with embodiments of the present disclosure.

FIG. 9 are images generated by an example SLO-OCT handheld probe in accordance with embodiments of the present disclosure. The SNR of the OCT system was 101 dB and the incident power on the eye for either SLO or OCT was 685 µW, which is under the ANSI maximum permissible exposure limit. The OCT axial resolution and 6 dB falloff range were measured to be 7 µm (in air) and 1.1 mm, respectively. Background measurements taken prior to imaging were subtracted from both SLO and OCT images to minimize static artifacts such as lens reflections and scratches or dust on optical elements. Such artifacts can be further reduced by the use of polarization gating. SLO images were acquired with a field of view of either 6.4°×8.8° as shown in the image labeled A, or 3° as shown in the images labeled B and C. Image A of FIG. 10 is a single frame SLO image taken at the maximum scan range of the MEMS scanner giving a 6.4°×8.8° FOV at a 4.4° eccentricity. Images B and C of FIG. 10 are single frame SLO images taken with a 3° FOV at a 5.7° and 3.8° eccentricity, respectfully, visualizing parafoveal photoreceptors.

At the smaller FOV, the SLO visualized parafoveal cones as close as a 3.8° eccentricity without adaptive optics. OCT images were acquired at a 6.4° FOV as shown in the image labeled D in FIG. 9. A mosaic of twenty-five 6.4°×8.8° FOV images was created using MosaicJ software to obtain a 26.4°×18.4° FOV image of the retina as shown in the image label E in FIG. 9. In the mosaic image, nerve fiber bundles can be clearly visualized at the bottom left region of the optic disc. Image D shows an OCT B-scan (10 frame average) spanning a 6.4° FOV at the fovea. Image E shows a mosaic with a 26.4°×18.4° FOV generated from 25 SLO images with the FOV of image A. Boxes 900, 902, and 904 indicate the locations of the SLO images A, B, and C, respectively. Dashed line 906 indicates the location of the OCT B-scan of image D.

FIG. 10 illustrates a diagram of another example probe 600 in accordance with embodiments of the present disclosure. The probe 600 may be used to image an eye as depicted in the figure. An optical pathway of the probe 600 is designated by reference number 1000. The probe 600 includes lenses L1-L7, which may be any suitable optical elements. In this example, lens L1 is an achromatic collimating lens. Lens L2 is an achromatic lens. Lenses L3-L7 together form a large FOV, high resolution telescope. The resolution of probe 600 when imaging an eye or model eye may be diffraction limited with an airy disk radius ranging between 11.8 μm and 13.1 μm. The RMS radius for the spot size when imaging an eye or model eye may be 6.7 μm.

Figure 11:
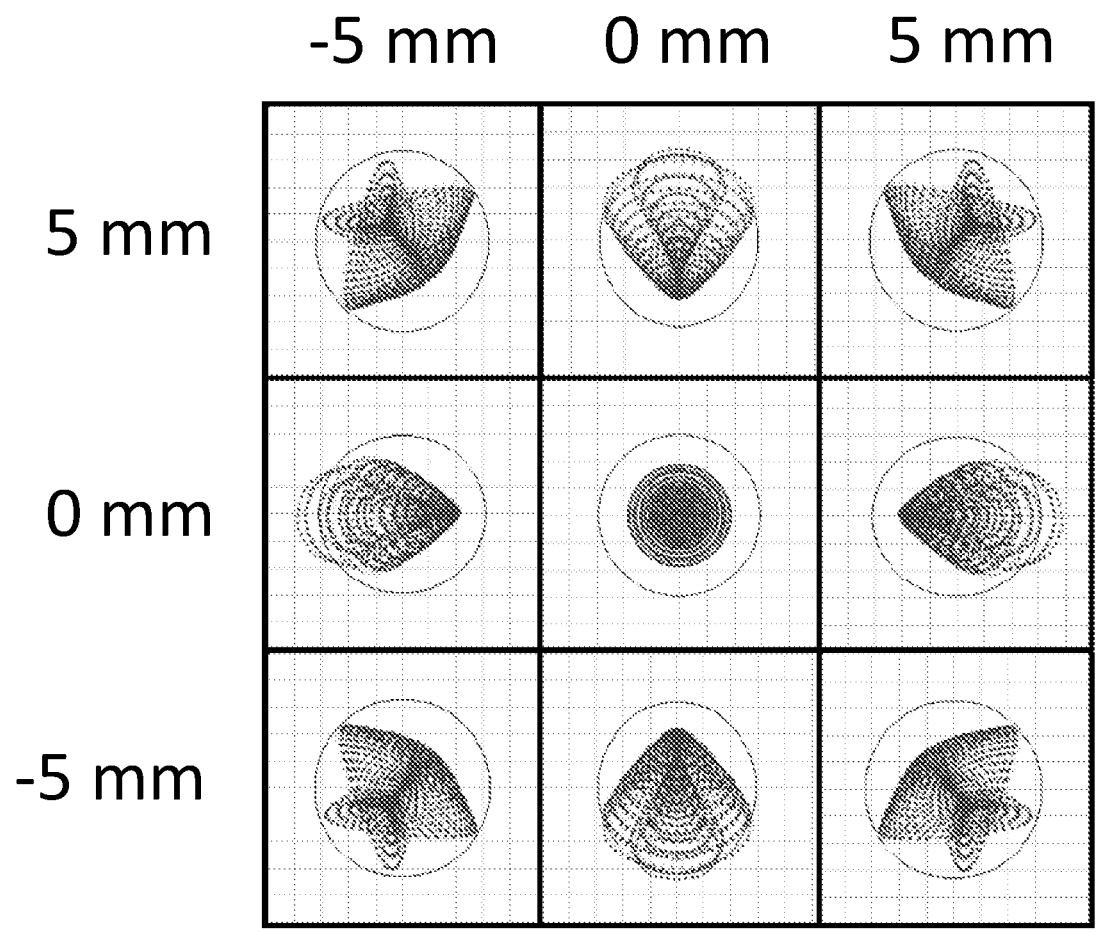
FIG. 11 depicts spot diagrams (grayscaled for 3 wavelengths spanning 1000-1100 nm) from the probe shown in FIG. 10 for OCT illumination on the retina of a model eye spanning a 10 mm FOV.

FIG. 11 depicts spot diagrams from the probe 600 shown in FIG. 10. These diagrams demonstrate diffraction-limited performance (12.5 um resolution) spanning the entire retinal field of view (10 mm×10 mm).

The presently disclosed subject matter provides, for example, a compact telescope design for constructing very compact SLO and OCT handheld probes with high imaging quality. A system in accordance with the present disclosure may be used for reducing the size of other devices that utilize both telescopes and light scanning such as bar scanners, laser printers, endoscopes, confocal microscopes, and the like.

Figure 12:
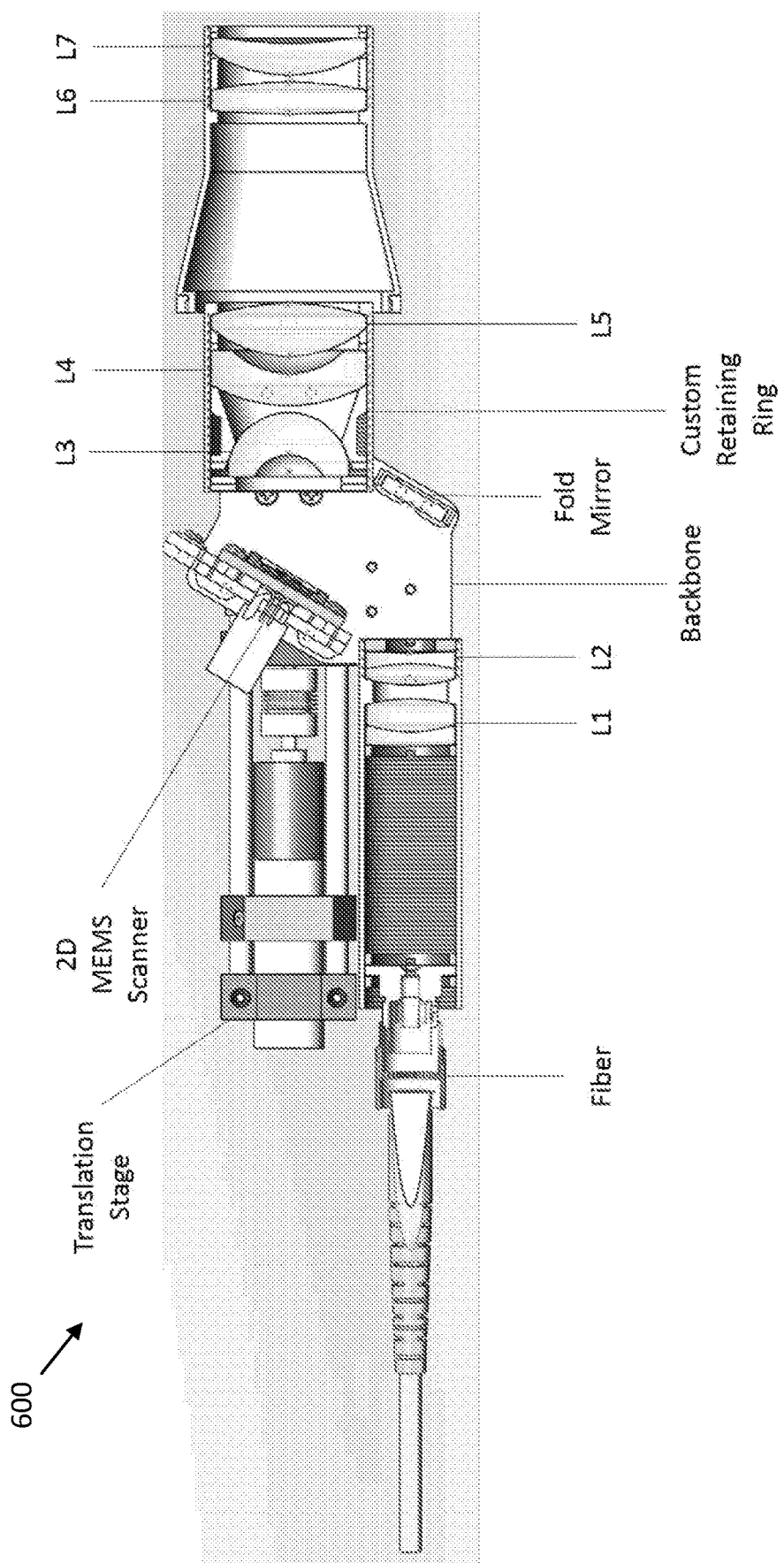
FIG. 12 is a cross-sectional side view of another example probe in accordance with embodiments of the present disclosure.

In accordance with embodiments of the present disclosure, FIG. 12 illustrates a cross-sectional side view of another example probe 600. The probe 600 shown in FIG. 12 has a very wide field of view. A prototype built in accordance with this design has a weight of 165 g, and the system was capable of a 35° FOV, which corresponds to a 10 mm FOV. The optical design for the probe 600 was used to specify component locations in the mechanical design. The mechanical design for the system was developed in SOLIDWORKS software. The probe 600 includes lens tubes, lens spacers, and mirror mounts for accommodating the closely spaced optics of the system and to maintain a small footprint. The internal skeleton and other structural components made of 7075 aluminum, in this example, to simplify fabrication and to maintain a low weight. The use of undersized dowel pins along with a tightly toleranced backbone provided for accurate component positioning, while the use of tangential and toroidal interfaces on pertinent lens surfaces minimized stress induced distortions of the optical wavefront. ZEMAX software was used to determine the maximum permissible positional error of optical components. A mechanical tolerance stack analysis was performed to ensure that the optical design specifications were satisfied given standard commercial mechanical fabrication tolerances. The probe 600 has auto-focus capability through the use of an electronically controllable translation stage which actuates all components posterior to the principal optical bore, thereby improving stability during adjustment of the focus. The probe 600 incorporates an apodization filter located after the collimation optics used herein to further improve the lateral resolution of the system. The same scheme may also be used in an SLO system in a separate illumination path or in a variety of other telescope applications to better control the spatial intensity distribution of the illumination pattern. Lenses L1-L7 are shown in FIG. 12. It should be understood that lenses L1-L7 can be replaced by any suitable optical elements or combination thereof.

The various techniques described herein may be implemented with hardware or software or, where appropriate, with a combination of both. Thus, the methods and apparatus of the disclosed embodiments, or certain aspects or portions thereof, may take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the presently disclosed subject matter. In the case of program code execution on programmable computers, the computer will generally include a processor, a storage medium readable by the processor (including volatile and non-volatile memory and/or storage elements), at least one input device and at least one output device. One or more programs may be implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed subject matter. When implemented on a general-purpose processor, the program code combines with the processor to provide a unique apparatus that operates to perform the processing of the presently disclosed subject matter.

Features from one embodiment or aspect may be combined with features from any other embodiment or aspect in any appropriate combination. For example, any individual or collective features of method aspects or embodiments may be applied to apparatus, system, product, or component aspects of embodiments and vice versa.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims. One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed:

1. A system comprising:
an optical coherence tomography (OCT) probe including a light scanner for imaging an object;
a first optical element having a first focal length $f_1$ for imaging or relaying an image of the object at the distance $f_1$ from the first optical element;
a second optical element having a second focal length $f_2$ and having an optical axis substantially aligned with an optical axis of the first optical element for receiving an image of the object from the first optical element and for focusing an output of the image at the scanner at the distance $f_2$ from the second optical element on a side that opposes the first optical element; and
wherein the first optical element and the second optical element are separated by a distance d, wherein d is defined as a distance of ±5% of $$f_1 + f_2 - \frac{f_1^2}{r},$$

wherein r is the finite radius of curvature of the wavefront of light located at the object or image of the object.

2. The system of claim 1, wherein the optical elements are lenses.

3. The system of claim 1, wherein the first optical element and the second optical element are biconvex lenses.

4. The system of claim 1, wherein the first optical element is a biconvex lens.

5. The system of claim 4, further comprising a plano-concave lens positioned between the first optical element and the second optical element, and having an optical axis substantially aligned with the optical axes of the first and second optical elements.

6. The system of claim 1, further comprising an eye positioned at the distance $f_2$ from the second lens.

7. The system of claim 1, wherein the light scanner is a microelectromechanical system (MEMS) scanner.

8. The system of claim 1, wherein the light scanner is operably connected to scanning laser ophthalmoscopy (SLO) equipment for imaging the subject.

9. The system of claim 1, wherein the light scanner is operably connected to scanning optical coherence tomography (OCT) equipment for imaging the subject.

10. The system of claim 1, wherein the light scanner is operably connected to scanning optical coherence tomography (OCT) equipment and laser ophthalmoscopy (SLO) equipment for imaging the subject.

11. The system of claim 1, wherein r is between 0 and infinity.

12. The system of claim 11, wherein r is between the value of $$\frac{f_1^2}{f_1 + f_2}$$

and the larger of $5f_1$ or $5f_2$.

13. The system of claim 1, further comprising a field flattening element to reduce field curvature induced by the system design.

14. The system of claim 13, wherein a field flattening element is located near an intermediate focal or image plane.

15. The system of claim 13, wherein a field flattening element is the closest optical element surface to an intermediate focal or image plane.

16. The system of claim 1, wherein the first and second elements are combined into a single optical element with focal length $$f' = \frac{f_1 f_2}{f_1 + f_2}.$$

17. The system of claim 1, wherein the first optical element and the second optical element are meniscus lenses.

18. The system of claim 17, further comprising one meniscus and two biconvex lenses positioned between the first optical element and the second optical element, and having an optical axis substantially aligned with the optical axes of the first and second optical elements.

* * * * *